US006933401B2

(12) United States Patent
Molock et al.

(10) Patent No.: US 6,933,401 B2
(45) Date of Patent: Aug. 23, 2005

(54) PROCESS FOR THE PRODUCTION OF VICINAL DIESTERS FROM EPOXIDES

(76) Inventors: Frank Molock, 1543 Wild Fern Dr., Orange Park, FL (US) 32003; Joseph R. Hepting, 1119 18th St., Port Huron, MI (US) 48060; Shivkumar Mahadevan, 1717 County Rd. 220, #1801, Orange Park, FL (US) 32003

( * ) Notice: Subject to any disclaimer, the term of this patent is extended or adjusted under 35 U.S.C. 154(b) by 0 days.

(21) Appl. No.: 10/610,262

(22) Filed: Jun. 30, 2003

(65) Prior Publication Data

US 2004/0267046 A1 Dec. 30, 2004

(51) Int. Cl.[7] .............................. C07F 7/04; C07F 7/08
(52) U.S. Cl. ..................................... 556/437; 556/465
(58) Field of Search ................................. 556/437, 465

(56) References Cited

U.S. PATENT DOCUMENTS

| 3,280,176 A | | 10/1966 | Meier et al. | |
| 3,676,398 A | | 7/1972 | Francis | |
| 4,139,513 A | * | 2/1979 | Tanaka et al. | ................. 522/99 |
| 4,139,548 A | * | 2/1979 | Tanaka et al. | ............... 556/437 |
| 4,139,692 A | * | 2/1979 | Tanaka et al. | ................. 522/99 |
| 4,235,985 A | * | 11/1980 | Tanaka et al. | ............... 526/279 |
| 4,908,274 A | | 3/1990 | Jachmann et al. | |
| 5,907,025 A | | 5/1999 | Brunelle | |
| 2002/0077491 A1 | | 6/2002 | Shipps et al. | |

FOREIGN PATENT DOCUMENTS

WO    WO 98/58500 A1    12/1998

OTHER PUBLICATIONS

A remarkable epoxide opening. An expeditious synthesis of vernolepin and vernomenin. Danishefsky, Samuel; Kitahara, Takeshi; Schuda, Paul F.; Etheredge, Sarah J. Dep. Chem., Univ. Pittsburgh, Pittsburgh, PA, USA. Journal of the American Chemical Society (1976), 98(10).

Corticosteroid analogs. XXI. Stereochemistry of opening of stereoisomeric oxides of 1–acetyl–4–tert–butyl–1–cyclohexene in the presence of ethyl hydrazinecarboxylate. Dobrynin, V. N.; Akhrem, A. A. N. D. Zelinskii Inst. Org. Chem., Moscow, USSR. tzvestiya Akademii Nauk SSSR, Seriya Khimicheskaya (1966), (11), 1969–74.

Lewis base–catalyzed addition of trialkylaluminum compounds to epoxides. Schneider, Christoph; Brauner, Jorg. Institut fur Organische Chemie, Gottingen, Germany. Eur. J. Org. Chem. (2001), (23), 4445–4450.

Total synthesis of capsanthin using Lewis acid–promoted regio– and stereoselective rearrangement of tetrasubstituted epoxide. Yamano, Yumiko; Ito, Masayoshi. Kobe Pharmaceutical University, Kobe, Japan. Chem. Pharm. Bull. (2001), 49(12), 1662–1663.

Stereochemistry control in the lewis acid mediated lactonization reaction of g,d–epoxy–b–silyloxy esters. Nacro, Kassoum; Gorrichon, Liliane; Escudier, Jean–Marc; Baltas, Michel. Lombardi Cancer Center, Georgetown University Medical Center, Washington, DC, USA. Eur. J. Org. Chem. (2001), (22), 4247–4258.

s–p Chelation–controlled chemoselective ring openings of epoxides. Asao, N.; Kasahara, T.; Yamamoto, Y. Graduate School of Science, Department of Chemistry, Tohoku University, Sendai, Japan. Tetrahedron Lett. (2001), 42(44), 7903–7905.

Applications of Lewis acids for the efficient syntheses of diltiazem, cephems and taxoids. Hashiyama, Tomiki. Medicinal Chemistry Department, Discovery Research Laboratory, Tanabe Seiyaku Co Ltd, Toda, Saitama 335–8505, Jordan. Abstr. Pap.—Am. Chem. Soc. (2001), 221st ORGN–468.

Regio– and stereoselective synthesis of nor–nonactinic acid derivatives. Kinetic reaction control in the Lewis acid mediated domino reaction of 1,3–dicarbonyl dianions with 1–bromo–2,3–epoxypropanes. Langer, Peter; Freifeld, Ilia. Institut fur Organische Chemie der Georg–August–Universitat Gottingen, Gottingen, Germany. Chem.—Eur. J. (2001), 7(3), 565–572.

AlCl3 as an efficient Lewis acid catalyst in water. Fringuelli, F.; Pizzo, F.; Vaccaro, L. Dipartimento di Chimica, Universita Perugia, Perugia, Italy. Tetrahedron Lett. (2001), 42(6), 1131–1133.

Benzyloxymethyl group as a convertible internal ligand for La(OTf)3–catalyzed 7–endo ring–opening of hydroxy epoxide. Fujiwara, Kenshu; Morishita, Hiroshi; Tokiwano, Tetsuo; Murai, Akio. Division of Chemistry, Graduate School of Science, Hokkaido University, Sapporo, Japan. Heterocycles (2001), 54(1), 109–110.

Assessment of the negative factors responsible for the decrease in the enantioselectivity for the ring opening of epoxides catalyzed by chiral supported Cr(III)–salen complexes. Gigante, Barbara; Corma, A.; Garcia, Hermenegildo; Sabater, Maria J. INETI, DTIQ Estrada do Paco do Lumiar, Lisbon, Port. Catal. Lett. (2000), 68(1,2), 113–119.

Indium metal and its halides in organic synthesis. Ranu, Brindaben C. Department of Organic Chemistry, Indian Association for the Cultivation of Science, Calcutta, India. Eur. J. Org. Chem. (2000), (13), 2347–2356.

(Continued)

*Primary Examiner*—J. Parsa
*Assistant Examiner*—Chukwuma Nwaonicha

(57) ABSTRACT

The present invention relates to a process comprising the steps of reacting in the presence of an epoxide opening catalyst, a substituted epoxide, and preferably a silicone containing substituted epoxide with at least one carboxylic acid and at least one protecting agent to form a vicinal dialkyl ester or a vicinal disilyl ester.

10 Claims, No Drawings

OTHER PUBLICATIONS

Synthesis of C–glycosylic compounds using three–membered cyclic intermediates. Smoliakova, Irina P. Chemistry Department, University of North Dakota, Grand Forks, ND, USA. Curr. Org. Chem. (2000), 4(6), 589–608.

Lewis acid–catalyzed regiospecific opening of vinyl epoxides by alcohols. Prestat, Guillaume; Baylon, Christophe; Heck, Marie–Pierre; Mioskowski, Charles. CEA–CE Saclay, Service des Molecules Marquees, Department de Biologie Cellulaire et Moleculaire, Gif sur Yvette, Fr. Tetrahedron Lett. (2000), 41(20), 3829–3831.

A platinum complex–catalyzed reaction of 3–chloro–1,3–diene monoepoxides with carbon nucleophiles involving nucleophilic substitution at the central carbon atom of the p–allyl ligand in the intermediate complex. Dependency of regioselectivity upon the added lewis acids. Kadota, Joji; Chatani, Naoto; Murai, Shinji. Department of Applied Chemistry, Faculty of Engineering, Osaka University, Suita, Japan. Tetrahedron (2000), 56(15), 2231–2237.

Dramatic rate acceleration in titanocene catalyzed epoxide openings: cofactors and Lewis acid co–catalysis. Gansauer, Andreas; Bluhm, Harald. Institut fur Organische Chemie der, Georg–August–Universitat, Gottingen, Germany. Chem. Commun. (Cambridge) (1998), (19), 2143–2144.

Lewis acid–mediated ring opening of propargylic epoxides: a stereospecific synthesis of 1,2–disubstituted homopropargylic alcohols. Bernard, Nicolas; Chemla, Fabrice; Normant, Jean F. Laboratoire Chimie Organo–Elements, CNRS, Universite Pierre Marie Curie, Paris, Fr. Tetrahedron Lett. (1998), 39(37), 6715–6718.

Ionic complex of VO2+ as a catalytic for the alcoholysis of epoxides and unsaturated ketones. Nikitin, Alexander V.; Kholuiskaya, Svetiana N.; Rubailo, Valentin L. Institute of Chemical Physics, Russian Academy of Science, Moscow, Russia. J. Chem. Biochem. Kinet. (1997), 3(1), 37–44.

Stereoselective preparation of five and/or six membered ring hydroxylactones obtained by Lewis acid mediated reaction of g,d–epoxy–b–hydroxyesters; access to 5–methylated 2–deoxy sugars. Nacro, Kassoum; Baltas, Michel; Escudier, Jean–Marc; Gorrichon, Liliane. Synthese Physiochemie Organique, Univ. Paul Sabatier, Toulouse, Fr. Tetrahedron (1997), 53(2), 659–672.

On the mechanism of alcoholysis of allylic and benzylic alcohols and of epoxides in the presence of ceric ammonium nitrate. Chapuzet, Jean–Marc; Beauchemin, Sophie; Daoust, Benoit; Lessard, Jean. Centre Recherche Electrochimie Electrocatalyse, Univ. Sherbrooke, Sherbrook, PQ, Can. Tetrahedron (1996), 52(12), 4175–80.

High–Speed "Immortal" Polymerization of Epoxides Initiated with Aluminum Porphyrin. Acceleration of Propagation and Chain–Transfer Reactions by a Lewis Acid. Akatsuka, Masaki; Aida, Takuzo; Inoue, Shohei. Faculty of Engineering, University of Tokyo, Tokyo, Japan. Macromolecules (1994), 27(10), 2820–5.

Remarkable selectivity in Lewis–acid–induced ring opening of 5–acetyl–10,11–dihydro–10,11–epoxy–5H–dibenz[b,f] azepine. Haasz, Ferenc; Galamb, Vilmos. Alkaloida Chem. Co. Ltd., Tiszavasvari, Hung. J. Chem. Res., Synop. (1993), (12), 494–5.

Meso–epoxides in asymmetric synthesis: enantioselective ring opening by nucleophiles in the presence of chiral Lewis acids. Paterson, Ian; Berrisford, David J. Univ. Chem. Lab., Cambridge, UK. Angew. Chem. (1992), 104(9), 1204–5 (See also Angew. Chem., Int. Ed. Engl., 1992, 31(9), 1179–80).

Zeolite catalyzed ring opening of epoxides to acetylated diols with acetic anhydride. Ramesh, P.; Reddy, V. L. Niranjan; Venugopal, D.; Subrahmanyam, M.; Venkateswarlu, Y. Organic Chemistry Division–I, Indian Institution of Chemical Technology, Hyderabad, India. Synth. Commun. (2001), 31(17), 2599–2604.

Highly regioselective ring opening of epoxides and aziridines using cerium(III) chloride. Sabitha, G.; Satheesh Babu, R.; Rajkumar, M.; Reddy, C. S.; Yadav, J. S. Organic Division I, Indian Institute of Chemical Technology, Hyderabad, India. Tetrahedron Lett. (2001), 42(23), 3955–3958. CODEN: TELEAY ISSN: 0040–4039. Journal written in English.

Synthesis of multifunctionalized phosphonic acid esters via opening of oxiranes and azetidinium salts with phosphoryl–substituted carbanions. Bakalarz–Jeziorna, Agata; Helinski, Jan; Krawiecka, Boxena. Centre of Molecular and Macromolecular Studies, Polish Academy of Sciences, Lodz, Pol. J. Chem. Soc., Perkin Trans. 1 (2001), (9), 1086–1090.

Bis–chlorodibutyltin oxide as a new reagent for a mild, versatile and regioselective ring–opening of epoxides. Salomon, Claudio J. Departamento Farmacia, IQUIOS (CONICET), Facultad de Ciencias Bioquimicas y Farmaceuticas, Universidad Nacional de Rosario, Rosario, Argent. Synlett (2001), (1), 65–68.

Synthesis of Functionalized g–Spirolactone and 2–Oxabicyclo[3.3.0]octane Derivatives from Nucleophilic Oxirane Ring Opening. De los Santos, M. R.; Barreiro, E. J.; Braz–Filho, R.; Fraga, C. A. M. Departamento de Quimica, PPGQO, Universidade Federal Rural do Rio de Janeiro, Seropedica, Brazil. Tetrahedron (2000), 56(30), 5289–5295.

Fluorinated epoxides 5. Highly selective synthesis of diepoxides from a,w–diiodoperfluoroalkanes. Regioselectivity of nucleophilic epoxide–ring opening and new amphiphilic compounds and monomers. Cirkva, V.; Gaboyard, M.; Paleta, O. Technicka 5, Department of Organic Chemistry, Prague Institute of Chemical Technology, Prague, Czech Rep. Journal of Fluorine Chemistry (2000), 102(1–2), 349–361.

ron(III) trifluoroacetate as an efficient catalyst for solvolytic and nonsolvolytic nucleophilic ring opening of epoxides. Iranpoor, Nasser; Adibi, Hadi. Chem. Dep., Shiraz University, Shiraz, Iran. Bull. Chem. Soc. Jpn. (2000), 73(3), 675–680.

Selective ring–opening of w–epoxyalkyl (meth)acrylates. An efficient access to bifunctional monomers. Olszewski–Ortar, Agnes; Gros, Philippe; Fort, Yves. Laboratoire de Chimie Organique 1, Faculte des Sciences, associe au CNRS, INCM, Universite H. Poincare–Nancy–I, Vandoeuvre–les–Nancy, Fr. Tetrahedron Lett. (1997), 38(50), 8699–8702.

Regiochemical control of the ring opening of 1,2–epoxides by means of chelating processes. 10. Synthesis and ring opening reactions of mono– and difunctionalized cis and trans aliphatic oxirane systems. Azzena, Francesca; Calvani, Federico; Crotti, Paolo; Gardelli, Cristina; Macchia, Granco; Pineschi, Mauro. Dip. Chim. Bioorg., Univ. Pisa, Pisa, Italy. Tetrahedron (1995), 51(38), 10601–26.

Regiochemical control of the ring opening of 1,2–epoxides by means of chelating processes. 6. Opening reactions of 3,4–epoxytetrahydropyran. Chini, Marco; Crotii, Paolo; Gardelli, Cristina; Macchia, Franco. Dip. Chim. Bioorg., Univ. Pisa, Pisa, Italy. Tetrahedron (1994), 50(4), 1261–74.

One–pot synthesis of a,b–dihydroxy sulfides via titanium–promoted oxirane ring opening. Lin, Guoqiang; Shi, Zhicai; Zeng, Chunming. Shanghai Inst. Org. Chem., Chin. Acad. Sci., Shanghai, Peop. Rep. China. Tetrahedron: Asymmetry (1993), 4(7), 1533–6.

Oxirane ring–opening with alcohol catalyzed by organotin phosphate condensates. Complete inversion at tertiary and benzylic centers. Otera, Junzo; Niibo, Yoshihisa; Nozaki, Hitosi. Dep. Appl. Chem., Okayama Univ. Sci., Okayama, Japan. Tetrahedron (1991), 47(36), 7625–34.

Regiochemical control of the ring opening of 1,2–epoxides by means of chelating processes. 4. Synthesis and reactions of the cis– and trans–oxides derived from 3–[(benzyloxy)methyl]cyclohexene. Chini, Marco; Crotti, Paolo; Flippin, Lee A.; Gardelli, Cristina; Macchia, Franco. Dip. Chim. Bioorg., Univ. Pisa, Pisa, Italy. J. Org. Chem. (1992), 57(6), 1713–18.

iso–PrO)3TiX as novel reagents for regioselective oxirane ring opening. Raifel'd, Yu. E.; Nikitenko, A. A.; Arshava, B. M. Jt. Lab. Carbohydr. Nucleosides Synth., Moscow Inst. Fine Chem. Technol., Moscow, USSR. Tetrahedron: Asymmetry (1991), 2(11), 1083–4.

Ring–opening of oxiranes by silyl–substituted allyl anions. A regiochemical chameleon. Schaumann, Ernst; Kirschning, Andreas. Inst. Org. Chem., Univ. Hamburg, Hamburg, Fed. Rep. Ger. Tetrahedron Lett. (1988), 29(34), 4281–4.

Direct preparation of substituted olefins from epoxides utilizing lithium tetraalkylcerate. Ukaji, Yutaka; Fujisawa, Tamotsu. Chem. Dep. Resour., Mie Univ., Tsu, Japan. Tetrahedron Lett. (1988), 29(40), 5165–8.

Abstract, Database Beilstein 'Online!, Beilstein Institute for Organic Chemistry, Frankfurt–Main, DE; Database Accession No. RID8532044 and Boogaard, P.J. et al., Xenobiotica, vol. 29, No. 10, 1999, pp. 987–1008.

Abstract, Database Beilstein 'Online!, Beilstein Institute for Organic Chemistry, Frankfurt–Main, DE; Database Accession No. RID 2330074 and Chem. Lett, No. 2, 1992, pp. 231–234.

Abstract, Database Beilstein 'Online!, Beilstein Institute for Organic Chemistry, Frankfurt–Main, DE; Database Accession No. RID2881285 & Murakami, M. et al., HJetero-cycles, vol. 30, No. 1, 1990, pp. 567–581.

Abstract, Database Beilstein 'Online!, Beilstein Institute for Organic Chemistry, Frankfurt–Main, DE; Database Accession No. RID 2881348 and Arzneim Frosch. Stocs, P. et al., vol. 40, No. 1, 1990, pp. 13–18.

Abstract, Database Beilstein 'Online!, Beilstein Institute for Organic Chemistry, Frankfurt–Main, DE; Database Accession No. RID4824852.

Abstract, Database Beilstein 'Online!, Beilstein Institute for Organic Chemistry, Frankfurt–Main, DE; Database Accession No. RID4872647 Olszewski–Ortar, A. et al., Tetrahedron Lett, vol. 38, No. 50, 1997, pp. 8699–8702.

Abstract, Database Beilstein 'Online!, Beilstein Institute for Organic Chemistry, Frankfurt–Main, DE; Database Accession No. RID4069858 and Rev. Roum–Chim; Rosu & Cascaval, vol. 39, No. 8, 1944, pp 979–984.

* cited by examiner

PROCESS FOR THE PRODUCTION OF VICINAL DIESTERS FROM EPOXIDES

FIELD OF THE INVENTION

The present invention relates to processes for the production vicinal diesters.

BACKGROUND OF THE INVENTION

Various silicone containing monomers have found utility as starting materials in the production of medical devices, such as ophthalmic devices and particularly, soft contact lenses having improved permeability to oxygen. One class of suitable monomers includes tris and bis (trimethylsilyloxy)silylalkylglycerol methacrylates ("SiAGMA"). During the synthesis of SiAGMA certain diester acrylate impurities are also generated. The diester acrylates or free radical reactive difunctional groups act as crosslinkers during the polymerization of the SiAGMAs with other polymer forming components. Accordingly, the concentration of the diester acrylates must be controlled to ensure that the mechanical properties of the resulting medical device do not vary to an unacceptable degree.

Classical methods for preparing 1,2-diesters involve the treatment of 1,2-diols with acid chlorides or anhydrides in the presence of a base. However, functional groups such as trimethylsilyl ethers are sensitive to such conditions and additional purification is required to obtain the desired product(s) in high purity. One method for the production of vicinal diesters use an amine to catalyze the nucleophilic opening of the epoxide in the presence of an anhydride and methacrylic acid to form a partially acylated mixture of compounds containing a vicinal methacrylate. The difunctional free radical impurities that are made during the course of producing the monofunctional free radical reactive monomer have to be controlled using either a different synthetic pathway or the use of various purification steps. The free radical reactive functional groups in the monomeric materials are made and then rely heavily on various modes of post synthesis purification methodology.

Accordingly, there remains a need in the art for a process which can produce vicinal diesters in high yield and purity.

SUMMARY OF THE INVENTION

The present invention relates to a process comprising the steps of reacting, in the presence of a epoxide opening catalyst, a substituted epoxide, and preferably a silicone containing substituted epoxide with at least one carboxylic acid and at least one protecting agent to form a vicinal dialkyl ester or a vicinal disilyl ester. More specifically, the present invention relates to a process comprising the steps of reacting a substituted epoxide with at least one epoxide opening catalyst, at least one carboxylic acid, at least one protecting agent and at least one inhibitor at a temperature above about 60° C. for at least about 4 hours to form a compound of Formula VI or VII:

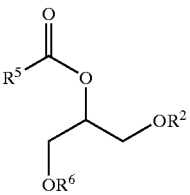
Formula VI

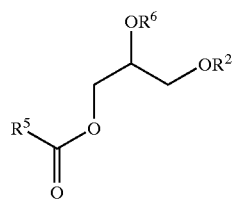
Formula VII wherein $R^2$ is any group which reacts more slowly with an oxygen containing nuclueophile as compared to said epoxide, $R^5$ is a straight or branched alkyl and alkenyl groups having 1 to 10 carbon atoms and $R^6$ is a residue of said protecting group which is capable of forming an ester or ether linkage. The vicinal dialkyl ester or a vicinal disilyl ester which are formed by the process of the present invention are useful as polymerization components for biomedical devices, and particularly for ophthalmic devices such as contact lenses.

DESCRIPTION OF THE INVENTION

Suitable substituted epoxides include those of Formula I, below:

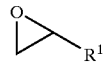

Wherein $R^1$ is any substituent which reacts more slowly with an oxygen containing nuclueophile as compared to the epoxide moiety. Preferred substituted epoxides include those shown in Formula II

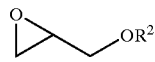

Wherein $R^2$ is any group which reacts more slowly with an oxygen containing nuclueophile as compared to the epoxide moiety. Examples of suitable $R^2$ groups include esters, amides, substituted and unsubstituted alkyls, siloxanes, ethers and the like. Specific, non-limiting examples include C1 to 3 alkyls substituted with at least one Si containing substituent and preferably at least one silicone linkage. Specific examples of suitable substituted epoxides include those of formula III:

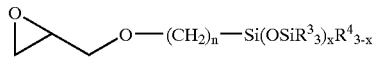

Wherein $R^3$ and $R^4$ are independently selected from alkyl groups having 1 to 3 carbon atoms, n is 1 to 3 and x is 0 to 3. Even more specifically, the substituted epoxide may be glycidoxypropyl heptamethyltrisiloxane.

Epoxides may be formed in a number of ways including, but not limited to, oxidation of alkenes with peroxyacids, formation by an intramolecular $S_N2$ reaction in which there is a trans halohydrin moiety, addition of a nucleophilic oxidizing agent (such as a basic solution of hydrogen peroxide) to an α,β-unsaturated carbonyl compound, and the reaction of a sulfonium ylide with a carbonyl compound. Alternatively, epoxides substituted with a Si containing group may be prepared by the hydrosilylation of an already formed epoxide containing an allyl functionality. Such methods are well known to those skilled in the art and this list of synthetic routes to epoxides and epoxides substituted with a Si containing group, in no way limits the scope of this invention to these preparations.

According to the process of the present invention the substituted epoxide is reacted with at least one soluble carboxylate salt, $R^5CO_2X$, at least one carboxylic acid $R^5CO_2H$ and at least protecting agent which can block reaction of free radical reactive species with a hydroxyl group. Suitable protecting agents include anhydrides, trimethylsilylchloride, allyl halide and the like. Anhydrides are preferred protecting agents. Suitable anhydrides include those having the formula $R^5CO_2OCR^5$. $R^5$ may be the same or different, and may be selected from straight or branched alkyl and alkenyl groups having 1 to 10 carbon atoms. Preferably $R^5$ is selected from alkenyl groups having 1-5 carbon atoms, and more preferably vinyl, styryl, allyl. Preferably $R^5$ is the same in the carboxylate salt, carboxylic acid and protecting agents.

The protecting agent reacts with the hydroxyl group after the carboxylate salt has opened the oxirane ring, keeping the metal alkoxide group from displacing the carboxy group from the carboxylic acid, and limits the OH reaction with other reactive species present in the reaction mixture. Thus, the use of a protecting agent allows for the production of the desired product in purities in excess of 80%, prior to any purification.

The epoxide opening catalyst used in the first step of the present invention may be any catalyst which is known in the art to open the epoxide ring. Suitable epoxide opening catalysts include Lewis acids, Lewis bases, Bronsted acids and porphyrin complexes, combinations thereof and the like. A preferred class of epoxide opening catalysts include carboxylate salts. For the carboxylate salt, suitable cations include alkali metals, such as Li, Na, K and ammonium. Preferably said cation is Li or Na, and preferred carboxylate salts include Li methacrylate and Na methacrylate. The epoxide opening catalyst should be soluble in the selected reaction solvent and at that the selected reaction temperature. The epoxide opening catalyst is added in an amount sufficient to catalyze the reaction, and preferably in an amount up to about 0.5 equivalents, based upon the epoxide.

In a preferred embodiment the carboxylic acid is methacrylic acid, the protecting agent is an anhydride and preferably methacrylic acid anhydride and the epoxide opening catalyst is an alkali metal methacrylate.

The carboxylic acid in used in an amount between about 0.01 and about 0.2 molar equivalents and preferably between about 0.05 and about 0.15 about based upon the amount of epoxide.

The protecting agent is used in a slight excess, preferably in an amount between about 1 and 1.5 molar equivalents and preferably between about 1 and about 1.1 molar equivalents based upon the amount of epoxide.

The reaction mixture may also include an inhibitor. Any free radical inhibitor may be used and suitable non-limiting examples include MEHQ, BHT, phenothiazine, hydroquinones, mixtures thereof and the like. The initiator may be used in amounts between about 1 and about 1000 ppm, and more preferably between about 1 and about 750 ppm.

The carboxylic acid may be used in a slight excess as the solvent or any non-reactive solvent may be used. Suitable non-reactive solvents are those that do not contribute or detract from the desired reaction at the selected reaction conditions, and include, but are not limited to non-nucleophilic solvents such as DMF, benzene, THF, mixtures thereof and the like.

The reaction is conducted at elevated temperatures, preferably greater than about 60° C. and more preferably between about 80° C. and about 120° C.

Suitable reaction times include at least about 4 hours, preferably at least about six hours and more preferably between about 6 and about 15 hours. It will be appreciated by those of skill in the art the temperature and reaction time are inversely proportional, and that higher reaction temperatures may allow for decreased reaction times and vice versa. Also, other reaction conditions, which effect the reaction, such as catalyst concentration, may also be varied to vary the reaction time and temperature of the process of the present invention.

The product of the reaction is a compound of Formula VI or VII, below:

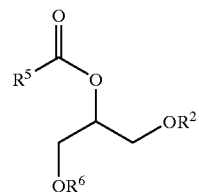

Formula VI

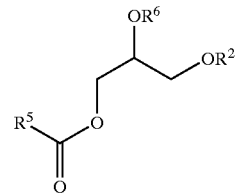

Formula VII wherein $R^2$, $R^5$ are as defined above and $R^6$ is a residue of the protecting group which is capable of forming an ester or an ether linkage.

In one embodiment the protecting agent is an anhydride and the product of the process of the present invention is a diester which contains siloxane moieties and has a purity of at least about 80%. The purity of the diester is further increased by treating a solution in hexanes with flash grade silica gel. The silica gel slurry is agitated (triturated) for a few hours and filtered to remove significant quantities of impurities that are more polar than the desired product. Alternatively, the purity of the vicinal diester may be increased by other purification such as supercritical fluid extraction.

Thus, the process of the present invention provides a one-pot tandem chemical transformation where an epoxide is first opened by reaction with a carboxylate and the resulting alcohol is rapidly trapped by the anhydride to form the desired vicinal diester. Many of the side reactions that occur due to the presence of hydroxyl groups and silicone moieties in the reaction mixture are avoided because the hydroxyl groups in the reaction mixture are short lived.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

EXAMPLE 1

The following reactants were charged to a dry 100 mL, 3 neck round bottom flask equipped with a magnetic stirrer, thermocouple, and a drying tube in the order and amounts listed below:

| | | |
|---|---|---|
| 1.47 g | lithium methacrylate (0.016 mole) | |
| 12.9 mg | butylated hydroxytoluene | |
| 16.17 g | methacrylic anhydride (0.105 mole) | |
| 17.20 g | methacrylic acid (0.2 mole) | |
| 33.60 g | glycidoxypropyl heptamethyltrisiloxane (0.1 mole) | |

The mixture was stirred vigorously, and heated to 100° C. for 7.5 hours. Once the reaction was complete, it was allowed to cool to ambient conditions, and transferred to a 500 mL separatory funnel.

The organics were diluted with 100 mL of hexanes, washed with 3×200 mL of 0.5N aqueous NaOH, followed with 3×100 mL of 2.5% aqueous NaCl. The organics were dried with 5.0 g of sodium sulfate, and the material was filtered over a fritted glass funnel.

The filtrate was treated with 15 g of silica gel, and the system was triturated for 3 hours. The organics were filtered over a fritted glass funnel, and the trituration was repeated using an additional 15 g of silica gel for another 3 hours. The desired product was isolated after filtration over a fritted glass funnel, followed by evaporation of volatile components at 55° C. under a vacuum pf<10 mbar. The purity of vicinal diester before and after trituration is shown in Table 1, below.

EXAMPLES 2–6

The reaction described in Example 1 was repeated; but the conditions were varied as shown in Table 1. The purity of the vicinal diester before & after trituration is also shown in Table 1.

We claim:
1. A process comprising the step of reacting glycidoxypropyl heptamethyltrisiloxane with at least one alkali metal methacrylate, methacrylic acid, methacrylic anhydride and at least one inhibitor at a temperature above about 60° C. for at least about 4 hours to form a compound having the following formula:

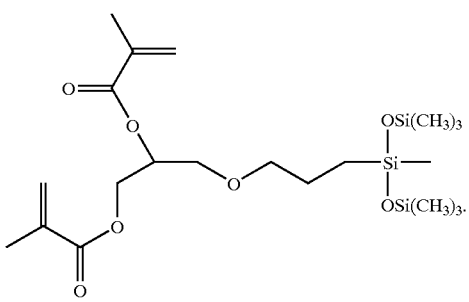

2. The process of claim 1 wherein said temperature is between about 80° C. and 120° C.

3. The process of claim 1 wherein said reacting step is conducted for a time between about 6 and about 15 hours.

4. The process of claim 1 wherein said alkali metal methacrylate comprises at least one cation selected from the group consisting of Li, Na and, K.

5. The process of claim 1 wherein said alkali metal methacrylate comprises Li methacrylate or Na methacrylate.

6. The process of claim 1 wherein said alkali metal methacrylate is added in an amount up to about 0.5 equivalents, based upon the glycidoxypropyl heptamethyltrisiloxane.

7. The process of claim 1 wherein said methacrylic acid in used in an amount between about 0.01 and about 0.2 molar equivalents based upon the amount of glycidoxypropyl heptamethyltrisiloxane.

8. The process of claim 1 wherein said methacrylic anhydride is used in an amount between about 1 and 1.5 molar equivalents based upon the amount of glycidoxypropyl heptamethyltrisiloxane.

9. The process of claim 1 wherein said selected from the group consisting of MEHQ, BHT, phenothiazine, hydroquinones and mixtures thereof.

10. The process of claim 1 wherein said initiator is used in amounts between about 1 and about 1000 ppm.

TABLE 1

| Ex. # | Temp. (° C.) | Methacrylic anhydride/ epoxide | Purity of Crude Material | Purity-1 trituation | Purity-2 trituations | Purity-4 trituations | Silica gel/epoxide per trituation | Epoxide scale (g) |
|---|---|---|---|---|---|---|---|---|
| 1 | 100 | 1.05 | 83.2 | | 89.9 | | 0.45 | 33.6 |
| 2 | 90 | 1.05 | 82.2 | | 89.6 | | 0.45 | 33.6 |
| 3 | 90 | 1.1 | 82.5 | | 89.4 | | 0.45 | 33.6 |
| 4 | 90 | 1.05 | | 82.4 | 86.3 | 89.2 | 0.25 | |
| 5 | 90 | 1.05 | 81.1 | | 87.8 | | 0.45 | 1000 |
| 6 | 100 | | | | 88.60 | | 0.45 | 500 |

* * * * *